(12) United States Patent
McArthur et al.

(10) Patent No.: US 11,648,353 B2
(45) Date of Patent: May 16, 2023

(54) INCREMENTAL SYRINGE AND RELATED SYSTEMS AND METHODS

(71) Applicant: Merit Medical Systems, Inc., South Jordan, UT (US)

(72) Inventors: Gregory R. McArthur, Sandy, UT (US); Richard P. Jenkins, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 331 days.

(21) Appl. No.: 16/986,973

(22) Filed: Aug. 6, 2020

(65) Prior Publication Data

US 2021/0038822 A1 Feb. 11, 2021

Related U.S. Application Data

(60) Provisional application No. 62/883,930, filed on Aug. 7, 2019.

(51) Int. Cl.
*A61M 5/315* (2006.01)

(52) U.S. Cl.
CPC ...... *A61M 5/3156* (2013.01); *A61M 5/31513* (2013.01); *A61M 2205/581* (2013.01); *A61M 2205/582* (2013.01)

(58) Field of Classification Search
CPC ............ A61M 5/3156; A61M 5/31513; A61M 5/31568; A61M 5/31573; A61M 5/31526; A61M 5/3158; A61M 5/178; A61M 2005/31508
See application file for complete search history.

(56) References Cited

U.S. PATENT DOCUMENTS

| 4,654,035 A | 3/1987 | Ando | |
|---|---|---|---|
| 2013/0197449 A1* | 8/2013 | Franklin | ........... A61M 5/31526 604/209 |
| 2016/0166772 A1* | 6/2016 | Mirzazadeh | ...... A61M 5/31595 604/222 |

FOREIGN PATENT DOCUMENTS

| WO | 2016094828 | 6/2016 |
|---|---|---|
| WO | 2019051315 | 3/2019 |

OTHER PUBLICATIONS

International Search Report and Written Opinion dated Nov. 13, 2020 for PCT/US2020/045204. , Nov. 13, 2020.
Gillespie, et al., A Tale of 2 Studies: A Biomechanical Comparison of Extrapelvic and Intrapelvic Fixation for Acetabular Fractures Among he Elderly and a Comparison of Dosage Accuracy and Precision for Traditional and Incremental Syringes, Doctoral Dissertation, Wake Forest University, pp. 5-6 figure 5 ,2016 ,1-69.

\* cited by examiner

*Primary Examiner* — Tasnim Mehjabin Ahmed
(74) *Attorney, Agent, or Firm* — Dorsey & Whitney LLP

(57) ABSTRACT

An incremental syringe configured for displacement of fluid, such as medicaments is disclosed. The syringe may comprise detents on the syringe plunger configured to provide tactile feedback, audible feedback, or both, for discrete units of fluid aspirated or injected to or from the syringe. In some embodiments, a second set of detents is included, and in some embodiments a third set of detents is included.

20 Claims, 7 Drawing Sheets

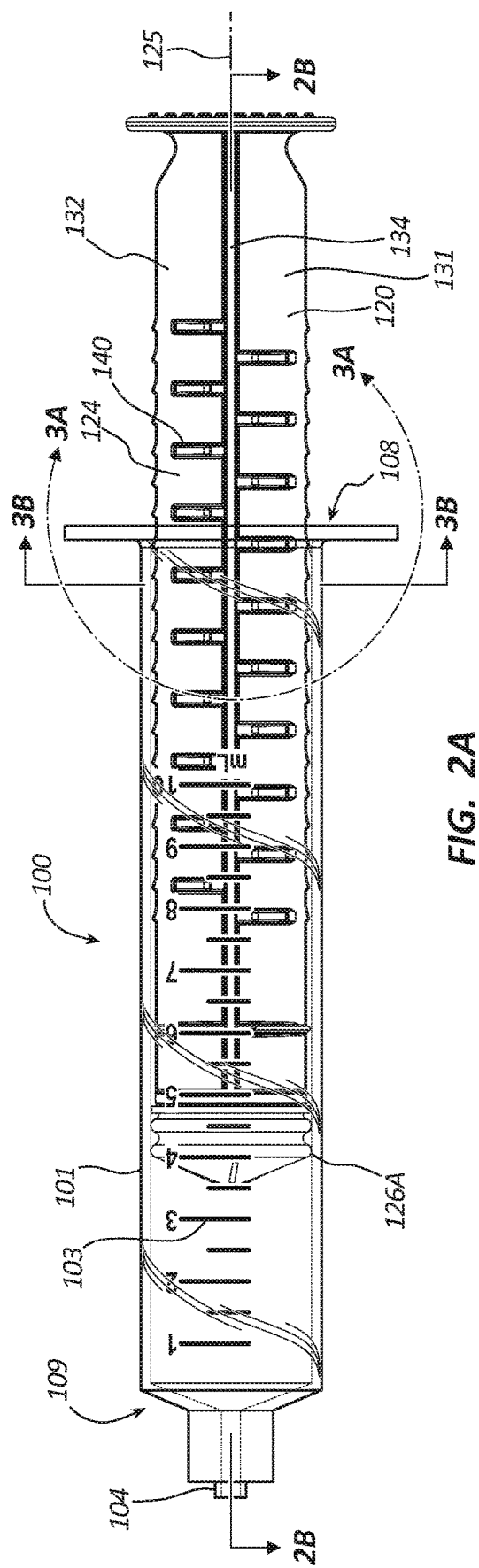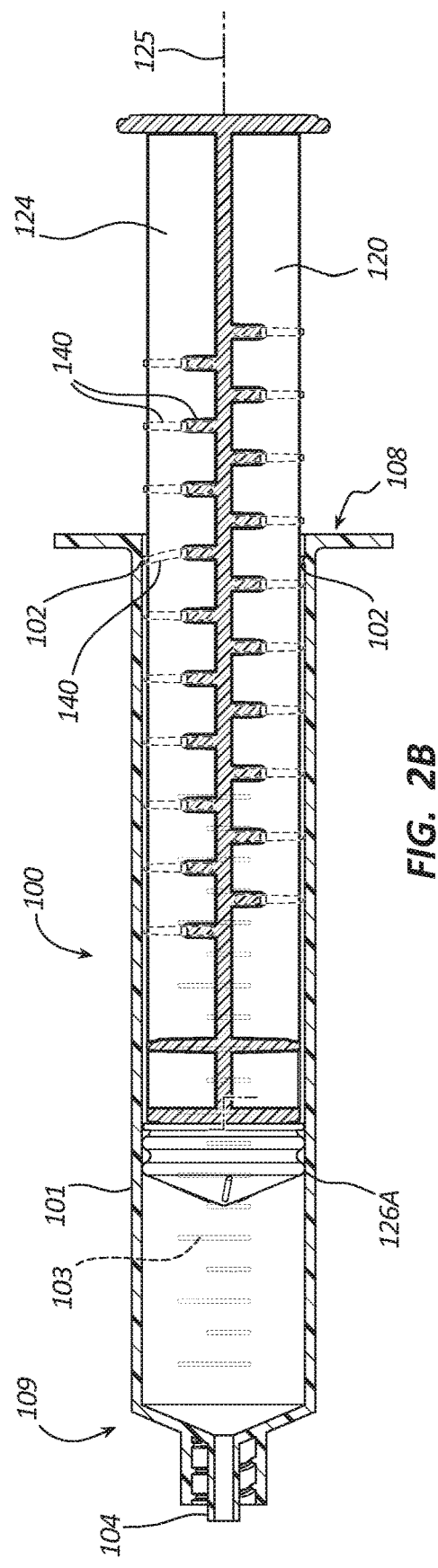
FIG. 2A
FIG. 2B

INCREMENTAL SYRINGE AND RELATED SYSTEMS AND METHODS

RELATED APPLICATIONS

This application claims priority to U.S. Provisional Application No. 62/883,930, filed on Aug. 7, 2019 and titled, "Incremental Syringe and Related Systems and Methods," which is hereby incorporated by reference in its entirety.

TECHNICAL FIELD

The present disclosure related generally to the field of medical devices. More particularly, the present disclosure relates medical syringes configured to provide audible and/or tactile feedback correlating to volumetric increments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2A is a top view of the syringe assembly of FIGS. 1A and 1B.

FIG. 2B is cross-sectional side view of the syringe assembly of FIG. 2A taken along section line 2B-2B.

DETAILED DESCRIPTION

Figures 1A, 1B:
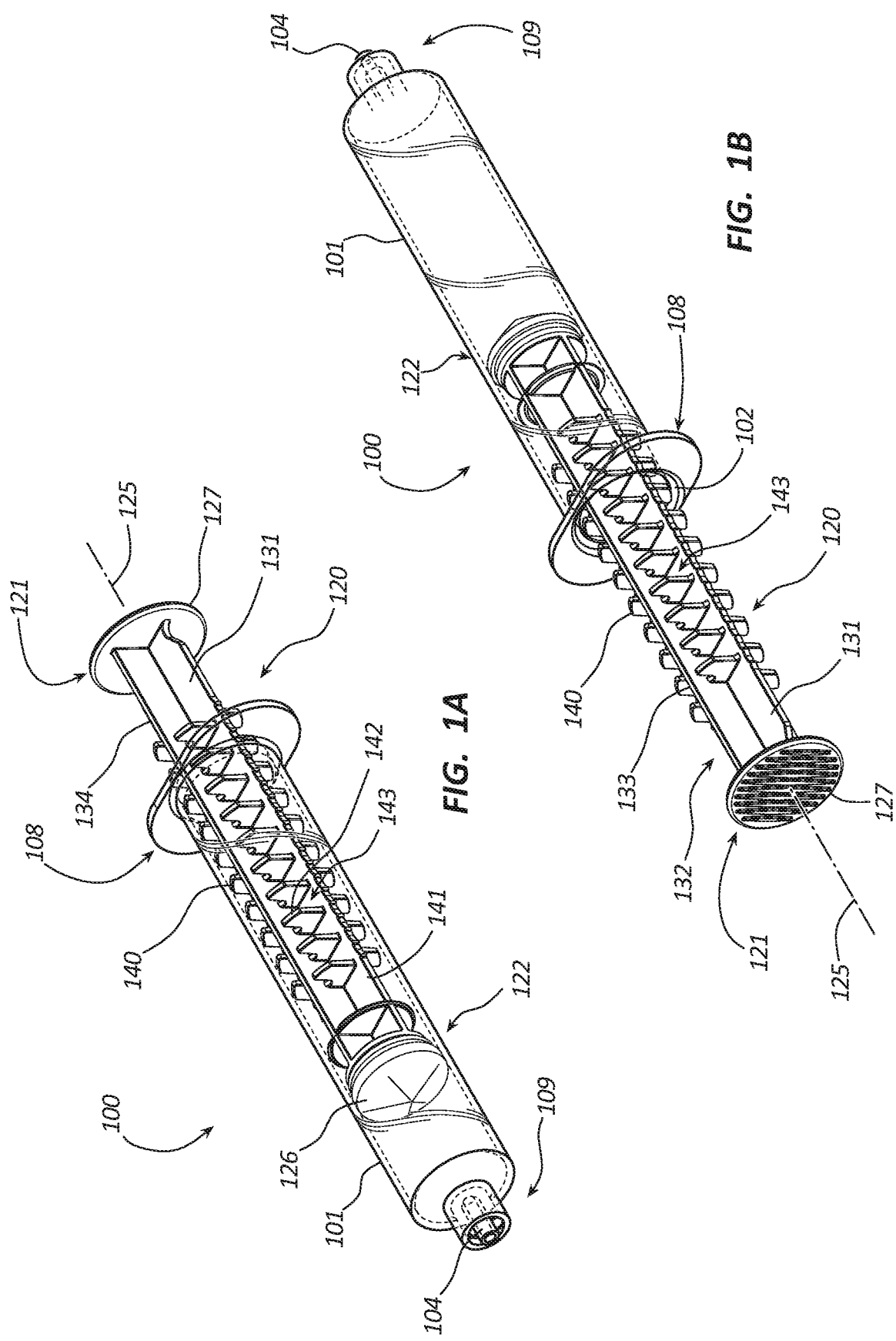
FIG. 1A is a perspective top view of a first embodiment of a syringe assembly.
FIG. 1B is a perspective bottom view of the syringe assembly of FIG. 1A.

The use of a syringe in the administration of an injection of medication may in some instances include complexities. For example, the during some procedures a syringe is first be filled to a desired volume from a medication vial. The filling process may include instances where the clinician pushing excess medication back into the vial until the plunger seal visually lines up with a predefined graduation mark indicating the desired volume. The variability of properties of syringes and medications (such as color) can in some instances add difficulty to the placement of the plunger on the desired graduation mark. The administration process may also have complexities. The clinician may, in some instances, desire to administer only a portion of the syringe volume. In such instances, visual indication of the plunger seal in reference to a graduation mark is also used to deliver the necessary volume of medication and to avoid over-delivery. Some therapies require multiple injections from a single filled syringe and, as such, create multiple opportunities for the injection of an incorrect volume. In other instances, visual observation by the clinician of other aspects of the therapy during the administration may be associated with a procedure. For example, the clinician may observe an instrument monitor or the injection site during the administration of the medication. In some embodiments, syringes configured to provide additional feedback regarding dosage and syringe position, including audible and tactile feedback, may facilitate filling and delivery of medicaments in desired volumes.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

Like numbers refer to like elements throughout. In the figures, the thickness of certain lines, layers, components, elements, or features may be exaggerated for clarity. The terminology used herein is for the purpose of describing particular embodiments only and is not intended to be limiting of the invention. As used herein, the terms "comprises" or "comprising," when used in this specification, specify the presence of stated features, integers, steps, operations, elements components, and/or groups or combinations thereof, but do not preclude the presence or addition of one or more other features, integers, steps, operations, elements, components, and/or groups or combinations thereof. Similarly, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

The phrase "coupled to" is broad enough to refer to any suitable coupling or other form of interaction between two or more entities, including mechanical, fluidic and thermal interaction. Thus, two components may be coupled to each other even though they are not in direct contact with each other. The phrases "attached to" or "attached directly to" refer to interaction between two or more entities which are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

Although the terms first, second, etc., may be used herein to describe various elements, components, regions, layers, and/or sections, these elements, components, regions, layers, and/or sections should not be limited by these terms. Rather, these terms are only used to distinguish one element, component, region, layer, and/or section from another element, component, region, layer, and/or section. Thus, a first element, component, region, layer, or section discussed herein could be termed a second element, component, region, layer, or section without departing from the teachings of the present disclosure. The sequence of operations (or steps) is not limited to the order presented in the claims or figures unless specifically indicated otherwise.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe, the proximal end of the syringe refers to the end nearest the flange and the distal end refers to the opposite end, the end nearest the inlet/outlet port of the syringe.

Figure 3A:
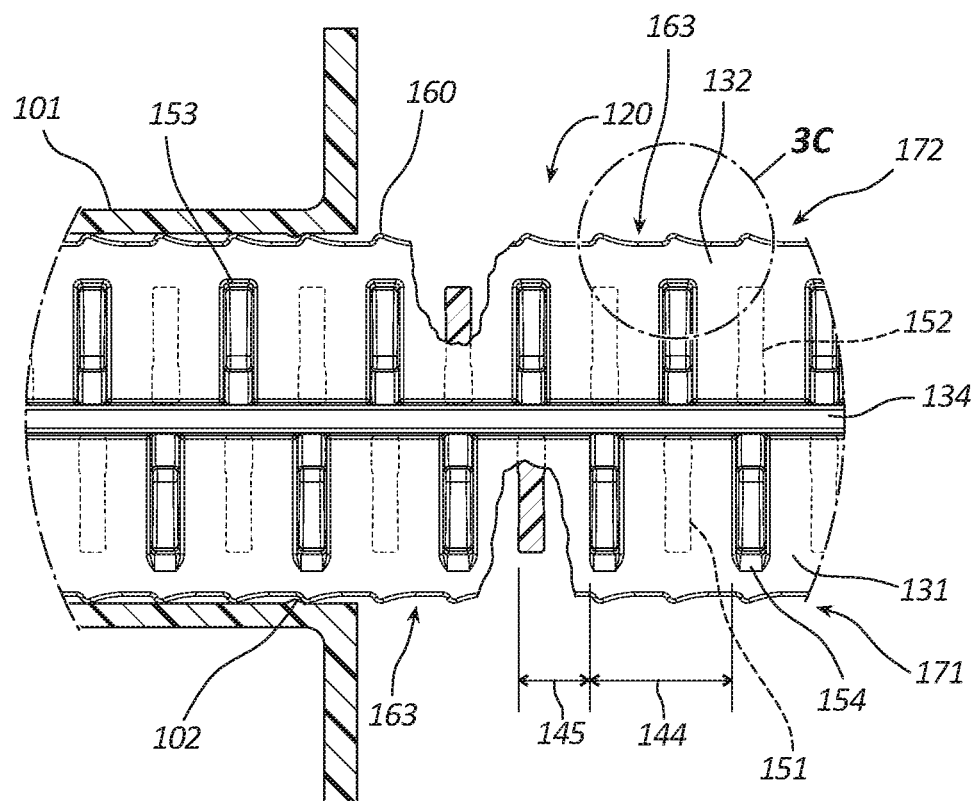
FIG. 3A is a detail view of a proximal portion of the syringe assembly of FIG. 2A.
Figure 3B:
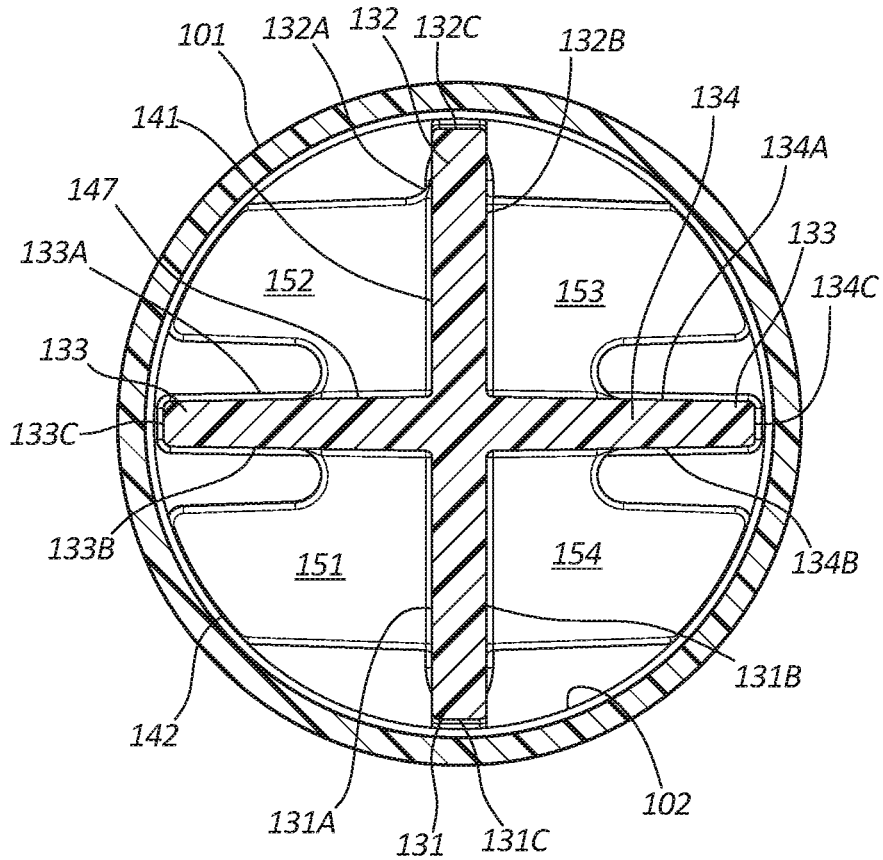
FIG. 3B is a cross-sectional end view of the syringe assembly of FIG. 2A taken along section line 3B-3B.
Figure 3C:
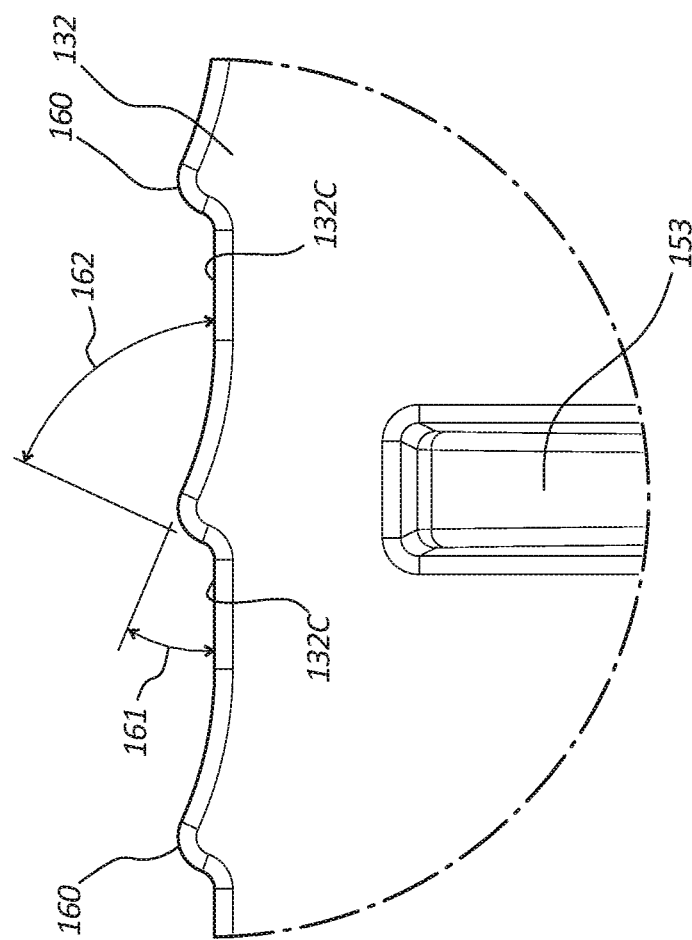
FIG. 3C is a detail view of a portion of a plunger of the syringe assembly of FIG. 3A.

FIGS. 1A, 1B, 2A, 2B, 3A, 3B, and 3C illustrate a first embodiment of the syringe assembly 100. FIG. 1A is a perspective top view of a first embodiment of the syringe assembly 100 and FIG. 1B is a perspective bottom view of the syringe assembly 100. As a note, in the views of FIGS. 1A and 1B, the graduation marks (103 of FIG. 2A) are not show for clarity when viewing other components such as the plunger 120. FIG. 2A is a top view of the syringe assembly 100 and FIG. 2B is cross-sectional side view of the syringe assembly 100 cut along section line 2B-2B as indicated in FIG. 2A. FIG. 3A is a detail view of a proximal portion of the syringe assembly 100 shown in FIG. 2A. FIG. 3B is a cross-sectional end view of the syringe assembly 100 cut along section line 3B-3B as indicated in FIG. 2A. FIG. 3C is a detail view of a portion of a plunger 120 of the syringe assembly 100 as shown in FIG. 3A.

As illustrated, the syringe assembly 100 comprises a syringe plunger 120 received within a syringe body 101 comprising a proximal end 108 and a distal end 109. The plunger 120 may include a seal 126 coupled to a distal end 122 and a flange 127 disposed at the proximal end 121. In the illustrated embodiment, the syringe body 101 includes a raised lip 102 disposed on an inside wall thereof adjacent the proximal end 108 and a syringe tip 104 at the distal end 109. The raised lip 102 may extend around the complete circumference of the syringe body 101 and may be configured to engage one or more features of the plunger 120. The raised lip 102 may take any suitable form, including a continuous ring, a ring interrupted by notches or gates, etc., and may have any suitable profile (e.g., half-circle, triangular, rectangular, etc.). The syringe body 101 may comprise a plurality of graduation marks 103 indicating volumetric increments. In the illustrated embodiment, the graduation marks 103 may indicate a volume within the syringe body 101 between a distal edge 126A of the seal 126 and the syringe tip 104. More specifically, a graduation mark 103 may indicate a specific volume when the distal edge 126A is longitudinally aligned with the graduation mark 103. For example, FIG. 2A illustrates the distal edge 126A aligned with a graduation mark 103 indicating 4 ml.

The seal 126 may be generally formed of a flexible organic polymer material (e.g., rubber, thermoplastic elastomer (or "TPE"), etc.) and may be removably or permanently coupled to the plunger 120 and configured to displace fluid within the syringe body 101. For example, displacement of the plunger 120 and seal 126 may displace a liquid pharmaceutical formulation from the syringe body 101 through the syringe tip 104. The syringe tip 104 may take any form suitable for coupling to a medical device, such as a Luer fitting.

The plunger 120 may comprise an elongate shaft 124 extending from the proximal end 121 to the distal end 122 defining a longitudinal axis 125 of the plunger 120. The elongate shaft 124 may further comprise features at the distal end 122 suitable for coupling of the seal 126 thereto.

The plunger 120 may comprise one or more longitudinal ribs extending radially away from the longitudinal axis 125. For example, in the illustrated embodiment, the plunger 120 includes a first rib 131, a second rib 132, a third rib 133, and a fourth rib 134 joined together along the longitudinal axis 125. As shown in FIG. 3B, the first rib 131 includes a first side 131A and a second side 131B opposite the first side 131A and an elongate edge 131C opposite the longitudinal axis 125. Similarly, the second rib 132, the third rib 133, and the fourth rib 134 include: first sides 132A, 133A, 134A; second sides 132B, 133B, 134B; and elongate edges 132C, 133C, 134C, respectively. The first rib 131 and the second rib 132 may be disposed in a first plane, and the third rib 133 and the fourth rib 134 may be disposed in a second plane orthogonal to the first plane. The first rib 131, second rib 132, third rib 133, and fourth rib 134 may be sized such that the elongate edges 131C, 132C, 133C, and 134C are disposed adjacent the raised lip 102 when the plunger 120 is disposed within the syringe body 101. In other words, the elongate edges 131C, 132C, 133C, and 134C may provide for slidable engagement of the plunger 120 with the syringe body 101 and/or raised lip 102, and may establish a limit of lateral displacement of the elongate shaft 124 relative to the syringe body 101.

With reference to FIGS. 1A-3C, the first rib 131, second rib 132, third rib 133, and fourth rib 134 may have the same thickness (distance between the first side and the second side) or different thicknesses. In some embodiments, the thickness of the first rib 131 and the second rib 132 may be greater than the thickness of the third rib 133 and the fourth rib 134. The thickness of each rib 131, 132, 133, 134 may be constant from the longitudinal axis 125 to the elongate edge 131C, 132C, 133C, 134C or tapered.

The plunger 120 may include a plurality of leaves or protrusions 140 extending radially away from the longitudinal axis 125. Each protrusion 140 may be formed of a cantilever flange or leaf and may be disposed within a plane substantially perpendicular to the longitudinal axis 125. In the illustrated embodiment, each protrusion 140 includes a base edge 141 coupled to the elongate shaft 124 and a perimeter edge segment 142 defining an engagement surface extending sufficiently away from the longitudinal axis 125 to interfere with the raised lip 102 of the syringe body 101. In other words, each protrusion 140 may cause a resistance to longitudinal displacement of the plunger 120 within the syringe body 101 due to engagement of the protrusion 140 with the raised lip 102. The resistance to longitudinal displacement of the plunger 120 may provide a audible and/or tactile feedback to the user. The perimeter edge segment 142 may be curved and extend around the longitudinal axis 125 along an arc, in some embodiments the arc may extend between 10 and 60 degrees, including between 10 and 40 degrees, between 10 and 30 degrees, and about 15 degrees. The perimeter edge segment 142 may have a radius of curvature substantially equal to an inside radius of the syringe body 101. The protrusions 140 may be positioned longitudinally along the plunger 120 such that when a protrusion 140 engages the raised lip 102 upon distal displacement of the plunger 120, the distal edge 126A of the seal 126 is aligned with a graduation mark 103.

The protrusions 140 may be formed of a structure that is flexible in the longitudinal direction, such that the perimeter edge segment 142 may deflect in the longitudinal direction upon engagement with the raised lip 102 (FIG. 2B). For example, as the plunger 120 is distally and/or proximally displaced within the syringe body 101, the perimeter edge segment 142 of the protrusion 140 may deflect in the opposite direction with respect to the plunger 120 upon engagement with the raised lip 102. Upon further displacement of the plunger 120, the perimeter edge segment 142 may deflect sufficiently to cause the perimeter edge segment 142 to displace inward toward the longitudinal axis 125 and away from the raised lip 102, allowing the perimeter edge segment 142 to distally pass by and disengage from the raised lip 102. Upon disengagement, the protrusion 140 may produce audible feedback (for example an audible click) and thus provide audible feedback to a user. Each protrusion 140 may also provide audible and/or tactile feedback upon displacement of the plunger 120 in the either direction.

As shown in FIGS. 3A and 3B, the plurality of protrusions 140 may be arranged in sets as described below. Each set may include a plurality of protrusions 140 arranged in a linear format parallel to and offset from the longitudinal axis 125. Each set may include a protrusion-free zone 143 in line with and between each pair of adjacent protrusions 140. In other words, the longitudinal space between adjacent protrusions 140 of one set may not include one or more protrusions 140 from another set. Each set of protrusions 140 may extend only partially around the longitudinal axis 125, for example, less than 90 degrees.

The illustrate embodiment comprises four sets of protrusions 140, a first set 151, a second set 152, a third set 153, and a fourth set 154. Other embodiments within the scope of this disclosure may comprise two sets of protrusions, three sets of protrusions, or more than four sets of protrusions. Regardless of the number of sets of protrusions 140, in some embodiments the protrusions may be evenly and equally spaced around the longitudinal axis 125. In other embodiments the sets may be disposed with different spacing. In some embodiments with two sets of protrusions 140, the sets of protrusions may be spaced and function according to the description of the illustrated embodiment below, with two sets of protrusions omitted. For example, the second set 152 and fourth set 154 may be omitted from the illustrated embodiment in an embodiment with two sets of protrusions.

In the illustrated embodiment, the plunger 120 may include a first set 151, a second set 152, a third set 153, and a fourth set 154 of protrusions 140. The first set 151, second set 152, third set 153, and fourth set 154 of protrusions 140 may be disposed angularly offset from each other around the longitudinal axis 125. The offset angle between adjacent sets may be equal or different. For the purposes of description, the first set 151, second set 152, third set 153, and fourth set 154 of protrusions 140 may be sequentially disposed around the longitudinal axis 125. In the illustrated embodiment, the offset angle between the first set 151 and the second set 152 may be different from the offset angle between the second set 152 and the third set 153. In the illustrated embodiment, the offset angle between the first set 151 and the second set 152 may be the same as the offset angle between the third set 153 and the fourth set 154. Similarly, the offset angle between the second set 152 and the third set 153 may be the same as the offset angle between the first set 151 and the fourth set 154.

The first set 151, second set 152, third set 153, and fourth set 154 of protrusions 140 may at least partially longitudinally overlap. In some embodiments, at least one protrusion 140 of each set is longitudinally positioned between adjacent protrusions 140 of at least one of the other sets. In other embodiments, at least one protrusion 140 of each set is longitudinally positioned between adjacent protrusions 140 of at least two of the other sets. In still other embodiments, at least one protrusion 140 of each set is longitudinally positioned between adjacent protrusions 140 of each of the other sets. In some embodiments, at least one protrusion 140 of each set is longitudinally aligned with at least one protrusion 140 of at least one of the other sets. In the illustrated embodiment, one protrusion 140 of each set may be aligned with only one protrusion 140 of one other set. In some embodiments, each protrusion 140 of each set may not be aligned with any protrusion 140 of any other set.

In the illustrated embodiment, each protrusion 140 of the first set 151 is aligned with a protrusion 140 of the third set 153 and each protrusion 140 of the second set 152 is aligned with a protrusion 140 of the fourth set 154. In the illustrated embodiment, the first set 151 and second set 152 of protrusions 140 may substantially longitudinally overlap such that all or all but one or two protrusions 140 of the first set 151 and the second set 152 may be longitudinally positioned between adjacent protrusions 140 of the second set 152 and the first set 151, respectively. Similarly, the third set 153 and fourth set 154 of protrusions 140 may substantially longitudinally overlap such that all or all but one or two protrusions 140 of the third set 153 and the fourth set 154 may be longitudinally positioned between adjacent protrusions 140 of the fourth set 154 and the third set 153, respectively.

The first set 151, second set 152, third set 153, and fourth set 154 of protrusions 140 may have equal spacing. In other words, the spacing distance 144 between adjacent protrusions 140 within each set may be constant equal and the spacing distance 144 the same for all sets. In the illustrated embodiment, the spacing distance 144 may be equal to one or the sum of two, three, four, or more volumetric increments, which increments may be indicated by the graduation marks 103. In the illustrated embodiment, the spacing distance 144 may be equal to the sum of volumetric increments or in other words two spacing distances between adjacent graduation marks 103. The second set 152 may be disposed longitudinally offset relative to the first set 151 by an offset distance 145 of one or the sum of two, three, four, or more spacing distances between adjacent graduation marks 103. In the illustrated embodiment, the second set 152 may be disposed longitudinally offset relative to the first set 151 by an offset distance 145 of one spacing distance 144 between adjacent graduation marks 103. In other words, the offset distance 145 between the first set 151 and the second set 152 is equal to one half of the spacing distance 144. As such, upon distal displacement of the plunger 120 within the syringe body 101, a protrusion 140 of the first set 151 and a protrusion 140 of the third set 153 may simultaneously engage the raised lip 102 whereupon the distal edge 126A is aligned with a graduation mark 103. The engagement of the protrusion 140 of the first set 151 and the protrusion 140 of the third set 153 may produce a resistance to displacement of the plunger 120, providing an audible and/or tactile feedback to the user. Upon further distal displacement of the plunger 120, the protrusion 140 of the first set 151 and the protrusion 140 of the third set 153 may each disengage the raised lip 102 and produce audible feedback (such as a click) and/or produce tactile feedback. Upon still further distal displacement, a protrusion 140 of the second set 152 and a protrusion 140 of the fourth set 154 may simultaneously engage the raised lip 102 whereupon the distal edge 126A is aligned with a graduation mark 103, and upon further distal displacement of the plunger 120, the protrusion 140 of the second set 152 and the protrusion 140 of the fourth set 154 may each disengage the raised lip 102 and produce audible feedback (such as a click) and/or produce tactile feedback.

Thus, as the plunger 120 is displaced, protrusions 140 from the sets may engage and disengage with the raised lip 102 creating audible and/or tactile feedback at intervals. Again, these intervals may correspond to measurements of volume and may correlate with graduation marks 103.

The protrusions 140 may be coupled to the first and second sides of the ribs. Each protrusion 140 may be coupled to a side of a rib along the base edge 141. Each protrusion 140 may also be at least partially coupled to a side of an adjacent rib along an inner edge 147. A non-coupled portion of the inner edge 147 may be disposed adjacent the side of the adjacent rib and may deflect distally and proximally with respect to the adjacent rib upon engagement with the raised lip 102 as shown in FIG. 2B.

For the purpose of clarity in description and not by way of limitation, the first side 131A and the first side 132A may be defined as facing the same direction and toward the third rib 133, and the second side 131B and the second side 132B may be defined as facing the same direction and toward the fourth rib 134. Similarly, the first side 133A and the first side 134A may be defined as facing the same direction and toward the second rib 132, and the second side 133B and the second side 134B may be defined as facing the same direction and toward the first rib 131.

As shown in FIG. 3B, in the illustrated embodiment, the base edge 141 of each protrusion 140 of the first set 151, second set 152, third set 153, and fourth set 154 is coupled to one of the first rib 131 and the second rib 132. More specifically, the base edge 141 of each protrusion 140 of the first set 151 may be coupled to the first side 131A of the first rib 131. Similarly, the base edge 141 of each protrusion 140 of the second set 152, the third set 153, and the fourth set 154 may be coupled to the first side 132A, the second side 132B, and the second side 131B, respectively. In the illustrated embodiment, the inner edge 147 of each protrusion 140 of the first set 151 may be partially coupled to the second side 133B of the third rib 133. Similarly, the inner edge 147 of each protrusion 140 of the second set 152, the third set 153, and the fourth set 154 may be coupled to the first side 133A, the first side 134A, and the second side 134B, respectively. As shown, the protrusions 140 may be shaped so as to be symmetrical to one another.

As illustrated in FIGS. 3A and 3C, the plunger 120 may comprise a plurality of edge protrusions 160. Each edge protrusion 160 may be disposed on one of the elongate edges 131C, 132C, 133C, and 134C. Each edge protrusion 160 may extend radially away from the longitudinal axis 125 sufficient to interfere with the raised lip 102. In other words, each edge protrusion 160 may cause a resistance to proximal and distal displacement of the plunger 120 within the syringe body 101 due to engagement of the edge protrusion 160 with the raised lip 102 and provide an audible and/or tactile feedback to the user. The edge protrusions 160 may be positioned longitudinally along the plunger 120 such that when an edge protrusion 160 engages the raised lip 102 upon distal displacement of the plunger 120, the distal edge 126A of the seal 126 is aligned with a graduation mark 103.

Thus, the protrusions 140 and edge protrusions 160 may be configured to provide audible and/or tactile feedback as the plunger 120 is displaced. In some embodiments at least one edge protrusion 160 is located at the same longitudinal position as each protrusion 140. Embodiments wherein some or all edge protrusions 160 are longitudinally offset from the protrusions 140 are likewise within the scope of this disclosure. While both the protrusions 140 and edge protrusions 160 may be configured to provide audible and/or tactile feedback, in some embodiments the protrusions 140 may provide more audible feedback than the edge protrusions 160 and the edge protrusions 160 may provide more tactile feedback than the protrusions 140. The interaction of these features, and the degree and type of feedback, may be related to the size, geometry, material, and other characteristics of the protrusions 140, edge protrusions, raised lip 102, and other portions of the syringe assembly 100.

The edge protrusions 160 may be shaped so as to provide different characteristics related to the resistance to displacement of the plunger 120 in the proximal direction and the distal direction. In other words, feedback to the user may be different in the distal direction vs. the proximal direction. For example, the shape of the edge protrusions 160 may provide difference tactile feedback depending on the direction the plunger 120 is displaced. The difference in tactile feedback may be defined by a difference in a proximal slope angle 161 vs. a distal slope angle 162. In the illustrated embodiment, the distal slope angle 162 may greater than the proximal slope angle 161. As such, the resistance to displacement of the plunger 120 produced by the edge protrusions 160 in the proximal direction may be more easily overcome by the user than the resistance to displacement in the distal direction.

The plurality of edge protrusions 160 may be arranged in sets as described below. Each set may include a plurality of edge protrusions 160 arranged along a single elongate edge of an elongate rib. Each set may include a protrusion-free zone 163 between each pair of adjacent edge protrusions 160. In other words, the longitudinal space between adjacent edge protrusions 160 of one set may not include one or more edge protrusions 160 of another set.

In the illustrated embodiment, the plunger 120 may include two sets of edge protrusions 160. In other embodiments, the plunger 120 may include one, three, or four sets of edge protrusions 160. A first set 171 of edge protrusions 160 may be associated with the first set 151 of protrusions 140. As such, each protrusion 140 of the first set 151 may be associated with an edge protrusion 160 of the first set 171.

In the illustrated embodiment, each protrusion 140 of the first set 151 may be configured to engage the raised lip 102 before the associated edge protrusion 160 of the first set 171 as the plunger 120 is displaced in the distal direction. For example, in some embodiments, the protrusion 140 may be configured to provide audible (such as a click) indicating the advancement of the plunger 120 by one increment, just before the associated edge protrusion 160 resists further advancement of the plunger 120. Thus, in the illustrated embodiment, each protrusion 140 may also disengage the raised lip 102 and produce audible feedback (such as a click) before the associated edge protrusion 160 engages the raised lip 102 as the plunger 120 is displaced in the distal direction. As such, the audible feedback (such as a click) may occur at the end of the volumetric increment confirming to the user that the intended delivery volume has been dispensed. The disengagement of each protrusion 140 before the engagement of the associated edge protrusion 160 may also provide for the plunger 120 to be constrained, trapped, or locked between the protrusion 140 and the associated edge protrusion 160 after the intended delivery volume has been dispensed. In other words, the edge protrusion 160 may provide a resistance to displacement of the plunger 120 in the distal direction, and the associated protrusion 140 may provide resistance to displacement of the plunger 120 in the proximal direction. The constrained, trapped, or locked position of the plunger 120 may correspond with a graduation mark.

In other embodiments, each protrusion 140 may engage the raised lip 102 substantially simultaneously with the associated edge protrusion 160 as the plunger 120 is displaced in the distal direction. Still in other embodiments, each protrusion 140 may engage the raised lip 102 after the associated edge protrusion 160 as the plunger 120 is displaced in the distal direction.

Thus, in some embodiments, the protrusions 140 may be configured to provide audible feedback (such as an audible click) and the edge protrusions 160 may be configured to provide tactile feedback (such as resistance to further advancement). Embodiments where the protrusions 140 and/or the edge protrusions 160 provide both audible and tactile feedback (for example, clicks that are both audible and tactile, resistance to advancement, etc.) are also within the scope of this disclosure.

In the illustrated embodiment, the first set 171 of edge protrusions 160 may also be associated with the second set 152 of protrusions 140. As such, each protrusion 140 of the second set 152 may be associated with an edge protrusion 160 of the first set 171. In the illustrated embodiment, each protrusion 140 of the second set 152 may substantially simultaneously engage the raised lip 102 with an edge protrusion 160 of the first set 171 as the plunger 120 is displaced in the distal direction. In other embodiments, each protrusion 140 of the second set 152 may engage the raised lip 102 before or after the associated edge protrusion 160 of the first set 171 as the plunger 120 is displaced in the distal direction.

In the illustrated embodiment, each edge protrusion 160 of the first set 171 may be associated with a protrusion 140 of the first set 151 or the second set 152. More specifically, adjacent edge protrusions 160 of the first set 171 may alternately be associated with a protrusion 140 of the first set 151 and the second set 152. As such, the number of edge protrusions 160 of the first set 171 may be equal to the sum of protrusions 140 of the first set 151 and the second set 152.

A second set 172 of edge protrusions 160 may also be associated with the first set 151 and the second set 152 of protrusions 140 similar to the first set 171 of edge protrusions 160 as described above. More specifically, the second set 172 may have the same number of edge protrusions 160 as the first set 171 and each edge protrusion 160 of the second set 172 may be longitudinally aligned with an edge protrusion 160 of the first set 171. In the illustrated embodiment, the first set 171 of edge protrusions 160 may be disposed along the first elongate edge 131C, and the second set 172 may be disposed along the second elongate edge 132C. In other embodiments, the first set 171 and the second set 172 of edge protrusions 160 may be disposed along the third elongate edge 133C and the fourth elongate edge 134C.

As stated above, the longitudinal placement of protrusions 140 and/or edge protrusions 160 along the elongate shaft 124 of the plunger 120 may be associated with volumetric increments of the syringe assembly 100, which may be indicated by the graduation marks 103 on the syringe body 101. A total measurable volume (ml) of the syringe assembly 100 as defined by the graduation marks 103 may be divided up into the volumetric increments (ml) as may be further defined by the graduation marks 103. In the illustrated embodiment, the syringe assembly may comprise a total measurable volume of 5 ml and volumetric increments of 0.25 ml. In other embodiments, the syringe may have a total measurable volume of from 1 ml to 60 ml, or more, with the protrusions 140 configured to divide the total measurable volume into at least 5, 10, 20, or more volumetric increments.

FIGS. 4A, 4B, 5A, and 5C illustrate a second embodiment of a plunger 220 that resembles the plunger 120 described above in certain respects. Accordingly, features that are the same are designated with the same reference numerals. Features that are different or new are designated with reference numerals beginning with "2." Relevant disclosure set forth above regarding similarly identified features thus may not be repeated hereafter. Moreover, specific features of plunger 120 shown in FIGS. 1A, 1B, 2A, 2B, 3A, 3B, and 3C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the plunger 220 in FIGS. 4A, 4B, 5A, and 5C. Any suitable combination of the features, and variations of the same, described with respect to the plunger 120 in FIGS. 1A, 1B, 2A, 2B, 3A, 3B, and 3C can be employed with the plunger 220 in FIGS. 4A, 4B, 5A, and 5C, and vice versa.

Figures 4A, 4B:
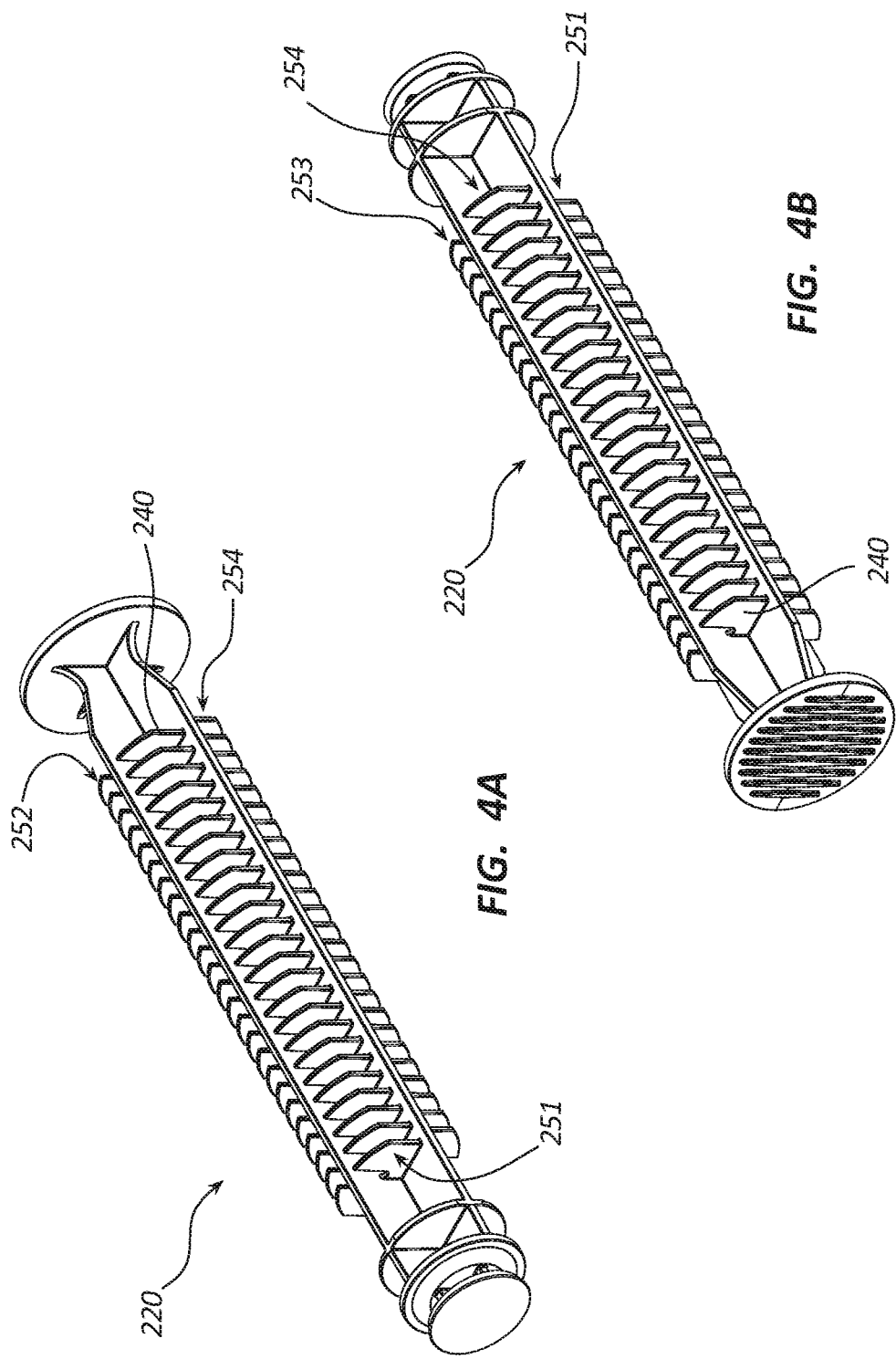
FIG. 4A is a perspective top view of another embodiment of a syringe plunger.
FIG. 4B is a perspective bottom view of the plunger of FIG. 4A.
Figure 5A:
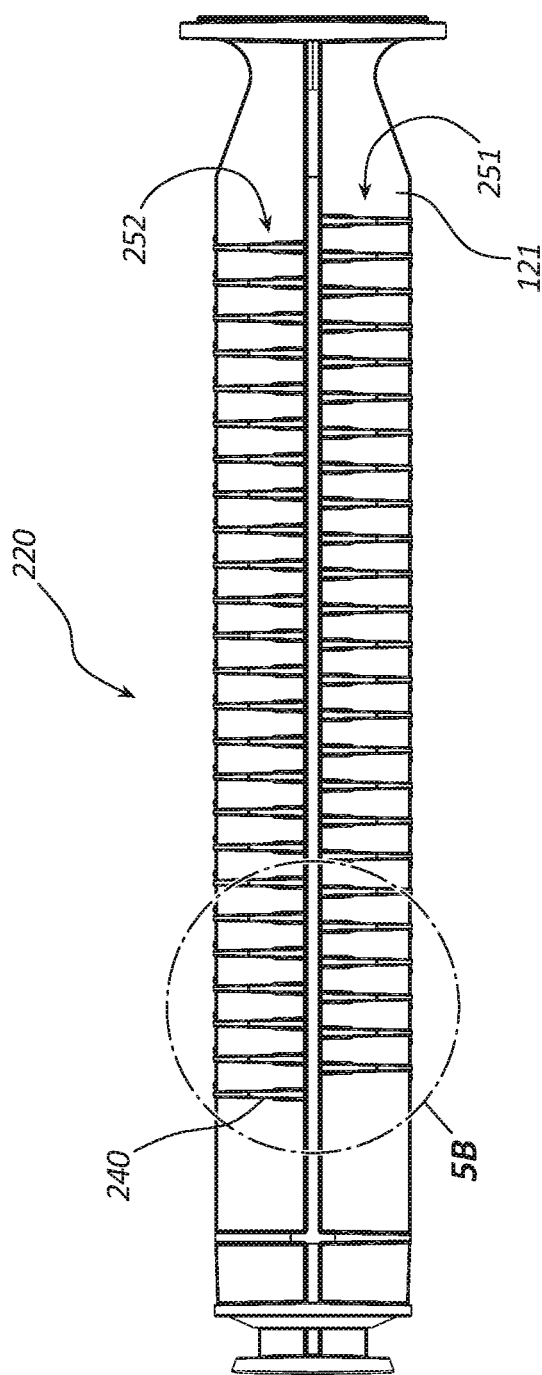
FIG. 5A is a top view of the plunger of FIG. 4A.
Figure 5B:
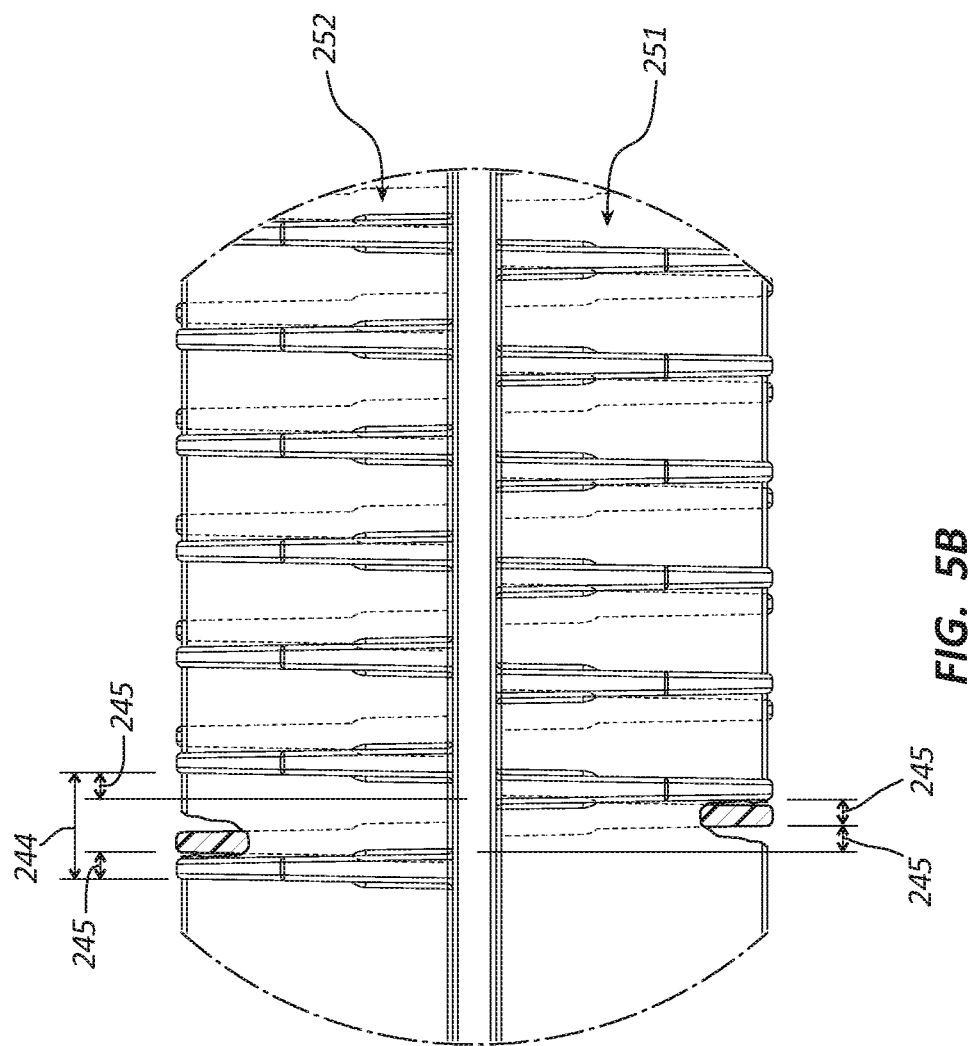
FIG. 5B is a detail view of a portion of the plunger of FIG. 5A.

FIGS. 4A and 4B are perspective top and bottom views, respectively, of a syringe plunger 220. FIG. 5A is a top view of the plunger 220 and FIG. 5B is a detail view taken from FIG. 5A of a portion of the plunger 220. While not shown, the plunger 220 may be used in conjunction with a syringe body similar to the syringe body 101 of FIGS. 1A, 1B, 2A and 2B, comprising a raised lip 102 and graduation marks 103. Similarly, while not shown, a seal 126 comprising a distal edge 126A may also be coupled to the plunger 220. As illustrated, the plunger 220 includes a first set 251, a second set 252, a third set 253, and a fourth set 254 of protrusions 240. The first set 251, second set 252, third set 253, and fourth set 254 of protrusions 240 may have constant spacing, and the spacing distance 244 between adjacent protrusions 240 within each set may be the same for all sets. As shown in FIG. 5B, in the illustrated embodiment, the spacing distance 244 between adjacent protrusions 240 within each set may be equal to one or the sum of two, three, four, or more volumetric increments, which increments may be indicated by the graduation marks 103. In the illustrated embodiment, the spacing distance 244 between adjacent protrusions 240 within each set may be equal to the sum of four spacing distances between adjacent graduation marks 103 indicating four volumetric increments. The first set 251, second set 252, third set 253, and fourth set 254 may be incrementally offset from each other in the longitudinal direction as shown in FIG. 5B. The offset distance 245 may be equal to one fourth of the spacing distance 244. As such, upon distal displacement of the plunger 220 within the syringe body, each protrusion 240 of the first set 251, second set 252, third set 253, and fourth set 254 may individually and in some embodiments incrementally engage the raised lip 102 whereupon the distal edge 126A is aligned with a graduation mark 103. In some embodiments, the engagement of each protrusion 240 with the raised lip 102 may produce a resistance to displacement of the plunger 220 and provide an audible and/or tactile feedback to the user. Upon further distal displacement of the plunger 220, each protrusion 240 may disengage the raised lip 102 and produce audible feedback (such as an audible click) and/or produce tactile feedback.

As stated above, the longitudinal placement of protrusions 240 along the elongate shaft of the plunger 220 may be associated with volumetric increments of a syringe assembly (such as syringe assembly 100), which may be indicated by graduation marks 103 on the syringe body 101 (see FIGS. 1A-3C). In the illustrated embodiment, the total measurable syringe volume may be 10 ml and the total measurable volume may be divided up into 100 volumetric increments of 0.1 ml. In other embodiments, the syringe assembly 100 may have a total measurable volume of from 1 ml to 60 ml, or more, with the protrusions (140 of FIGS. 1A-3C and 240 of FIGS. 4A-5B) configured to divide the total measurable volume into at least 5, 10, 20, 100, or more volumetric increments.

In all of the foregoing, the plunger or elongate shaft may comprise or consist of an organic polymer (e.g., polypropylene). Likewise, the syringe body may comprise or consist of an organic polymer (e.g., polypropylene). The seal (126 of FIG. 1A) may also be formed of an organic polymer, but generally a different material, that is elastic, such as natural or synthetic rubber or a thermoplastic elastomer (TPE).

Syringes according to the foregoing embodiments may be loaded with any suitable pharmaceutical formulation, such as a sterile injectable pharmaceutical formulation (e.g., a formulation comprising botulinum toxin or lidocaine in a pharmaceutically acceptable aqueous carrier) contained therein. In some embodiments, an injection needle (optionally with a removable or retractable cover to help minimize inadvertent "needle sticks") may be fixed to or operatively associated with the syringe tip (104 of FIG. 1A). Depending on the intended use, a rigid or flexible endoscope (e.g., a cystoscope) or guide cannula may be operatively coupled to the syringe outlet opening.

Use of the foregoing embodiments may include one or more of the following steps or processes. A user may fluidly access a container of medication and fill the syringe by proximally displacing the plunger beyond a defined graduation mark (103 of FIG. 2A) indicating a desired syringe volume during which one or more audible feedback indicia (such as audible clicks) and/or tactile responses are detected by the user. The user may then halt proximal displacement of the plunger upon the detection of a resistance to proximal displacement of the plunger. After filling the syringe to a volume greater than a desired injection volume, the user may distally displace the plunger during which one or more protrusions engage the raised lip and produce an audible and/or tactile feedback. The user may then halt distal displacement of the plunger in alignment with a graduation mark upon detection of a resistance to distal displacement of the plunger. In some instances, the halting of the distal displacement of the plunger at a desired graduation mark may be performed without visual observation of the plunger seal in relation to the graduation mark on the syringe body. In other words, the user may rely on the audible and/or tactile feedback to properly align the plunger seal with a graduation mark. The user may then fluidly access an injection site and inject medication by distally displacing the plunger to another defined graduation mark during which one or more audible feedback indicia (such as audible clicks) and/or tactile responses are detected by the user. The user may then halt the injection of medication upon the detection of a resistance to distal displacement of the plunger again relying on the resistance to displacement to align the plunger seal with the graduation mark. In some instances, the injection of a defined volumetric increment of medication may be performed without visual observation of the plunger seal in relation to the graduation marks on the syringe body. The user may then fluidly access another injection site with the same syringe and inject another defined volumetric increment of medication by distally displacing the plunger to another graduation mark during which one or more audible feedback indicia (such as audible clicks) and/or tactile responses are detected. The user may then again halt the injection of medication upon the detection of a resistance to distal displacement of the plunger without visual observation of the plunger seal in relation to the graduation mark on the syringe body relying again on the resistance to displacement to align the plunger seal with the graduation mark. The medication injection process may include multiple injections of defined volumetric increments during which audible and/or tactile feedback is detected by the user indicating the delivery of the volumetric increments. With each delivery of a volumetric increment, the user may halt injection upon detection of a resistance to displacement of the plunger.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Recitation in the claims of the term "first" with respect to a feature or element does not necessarily imply the existence of a second or additional such feature or element. Changes may be made to the details of the above-described embodiments without departing from the underlying principles of the present disclosure.

Further, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The invention claimed is:

1. A syringe, comprising:
    a body comprising a raised lip on an inside wall of the body; and a plunger disposed within the body, the plunger comprising:
        an elongate shaft comprising a longitudinal axis, a proximal end, a distal end and a plurality of elongate ribs;
        a seal;
        a flange disposed adjacent a proximal end; and
        a first set, a second set, a third set, and a fourth set of protrusions coupled to the elongate shaft,
        wherein each of the first set, the second set, the third set, and the fourth set of protrusions is disposed linearly along the longitudinal axis, wherein the first set, the second set, the third set, and the fourth set of protrusions are angularly offset around the longitudinal axis with respect to each other, wherein each of the first set, the second set, the third set, and the fourth set of protrusions comprises all protrusions disposed between a pair of the plurality of elongate ribs corresponding to that set;

wherein each protrusion extends so as to engage the raised lip upon longitudinal displacement of the plunger within the body, and wherein at least one protrusion of each set is longitudinally positioned between adjacent protrusions of at least one of the other sets.

2. The syringe of claim 1, wherein each protrusion is configured to produce an audible click upon disengagement with the raised lip.

3. The syringe of claim 1, wherein each protrusion is formed of a flexible leaf configured to longitudinally deflect upon engagement with the raised lip.

4. The syringe of claim 1, wherein a longitudinal spacing distance between adjacent protrusions is constant within each of the first set, second set, third set, and fourth set of protrusions, and wherein the longitudinal spacing distance is the same for first set, second set, third set, and fourth set.

5. The syringe of claim 4, wherein the first set, second set, third set, and fourth set of protrusions longitudinally overlap and are offset with respect to each other in the longitudinal direction by a distance of one quarter of the spacing distance.

6. The syringe of claim 4, wherein the first set, second set, third set, and fourth set of protrusions longitudinally overlap, wherein the first set and the second set of protrusions are offset with respect to each other in the longitudinal direction by an offset distance equaling one half of the spacing distance between adjacent protrusions, wherein the third set of protrusions is longitudinally aligned with one of the first set and the second set of protrusions, and wherein the fourth set of protrusions is longitudinally aligned with the other one of the first set and the second set of protrusions.

7. The syringe of claim 6, wherein the plunger further comprises a plurality of edge protrusions disposed along at least one of the plurality of elongate ribs, and wherein each edge protrusion is configured to engage the raised lip upon longitudinal displacement of the plunger within the body.

8. The syringe of claim 7, wherein each edge protrusion is configured to provide a resistance to longitudinal displacement of the plunger within the body upon engagement with the raised lip defining a tactile feedback to a user, and wherein when each edge protrusion engages the raised lip as the plunger is displaced in the distal direction, a distal sealing edge of the seal is in alignment with one of a plurality of graduation marks disposed on the body.

9. The syringe of claim 7, wherein each protrusion of the first set, second set, third set and fourth set of protrusions is associated with at least one edge protrusion.

10. The syringe of claim 7, wherein each edge protrusion comprises a proximal slope forming a first angle relative to the longitudinal axis and a distal slope forming a second angle relative to the longitudinal axis, and wherein the second angle is greater than the first angle.

11. A syringe plunger, comprising:

an elongate shaft comprising a longitudinal axis, a plurality of elongate ribs, a proximal end, and a distal end;

a flange disposed at the proximal end; and a first set, a second set, a third set, and a fourth set of protrusions coupled to the elongate shaft, wherein each of the first set, the second set, the third set, and the fourth set of protrusions is disposed linearly along the longitudinal axis, wherein the first set, the second set, the third set, and the fourth set of protrusions are disposed angularly offset around the longitudinal axis with respect to each other, wherein each of the first set, the second set, the third set, and the fourth set of protrusions comprises all protrusions disposed between a pair of the plurality of elongate ribs corresponding to that set, and wherein at least one protrusion of each set is longitudinally positioned between adjacent protrusions of at least one of the other sets.

12. The syringe plunger of claim 11, wherein each protrusion is configured to produce an audible click upon engagement with a portion of a syringe body.

13. The syringe plunger of claim 11, wherein each protrusion is formed of a flexible leaf configured to longitudinally deflect upon engagement with a portion of a syringe body.

14. The syringe plunger of claim 11, wherein a longitudinal spacing distance between adjacent protrusions is constant within each of the first set, second set, third set, and fourth set of protrusions, and wherein the longitudinal spacing distance is the same for first set, second set, third set, and fourth set.

15. The syringe plunger of claim 14, wherein the first set, second set, third set, and fourth set of protrusions longitudinally overlap, wherein the first set and the second set of protrusions are offset from each other in the longitudinal direction by an offset distance equaling one half of the spacing distance, wherein the third set of protrusions is longitudinally aligned with one of the first set and the second set of protrusions, and wherein the fourth set of protrusions is longitudinally aligned with the other one of the first set and the second set of protrusions.

16. The syringe plunger of claim 11, wherein the plunger further comprises a plurality of edge protrusions disposed along at least one of the plurality of elongate ribs, and wherein each edge protrusion is configured to engage a portion of a syringe body.

17. The syringe plunger of claim 16, wherein each edge protrusion is configured to provide a resistance to longitudinal displacement of the plunger within the syringe body upon engagement a raised lip defining a tactile feedback to a user, and wherein when each edge protrusion engages the raised lip as the plunger is displaced in the distal direction, the distal sealing edge is in alignment with one of a plurality of graduation marks disposed on the body.

18. The syringe plunger of claim 16, wherein each edge protrusion comprises a proximal slope forming a first angle relative to the longitudinal axis and a distal slope forming a second angle relative to the longitudinal axis, and wherein the second angle is greater than the first angle.

19. A method of using a syringe, comprising:
obtaining a syringe comprising:
- a body comprising a raised lip on an inside wall of the body; and
- a plunger disposed within the body, the plunger comprising:
  - an elongate shaft comprising a longitudinal axis, a proximal end, a distal end and a plurality of elongate ribs; and
  - three or more sets of protrusions disposed linearly along the longitudinal axis of the elongate shaft, each protrusion extending laterally away from the longitudinal axis so as to engage the raised lip upon longitudinal displacement of the plunger within the body,
  - wherein the three or more sets are disposed angularly offset around the longitudinal axis with respect to each other,
  - wherein each of the three or more sets of protrusions comprises all protrusions disposed between a pair of the plurality of elongate ribs corresponding to that set,
  - wherein each protrusion of at least two sets is configured to produce an audible click upon engagement with the raised lip, and
  - wherein the protrusions of at least two sets are arranged to alternately engage the raised lip upon longitudinal displacement of the plunger within the body;
fluidly accessing a container of medication;
proximally displacing the plunger beyond a defined graduation mark indicating a desired syringe volume during which one or more audible clicks are detected by the user;
distally displacing the plunger so that a distal edge of a plunger seal is aligned with a graduation mark;
fluidly accessing an injection site; and
distally displacing the plunger so that the distal edge is aligned with another graduation mark during which one or more audible clicks are detected by the user.

20. The method of claim 19, wherein at least one set of protrusions is configured to provide a resistance to longitudinal displacement of the plunger within the body upon engagement with the raised lip,
- wherein upon engagement of the raised lip as the plunger is distally displaced, the distal edge of the seal is aligned with a graduation mark, and
- wherein the method further comprises halting distal displacement of the plunger upon detection of the resistance by the user.

* * * * *